United States Patent
Kritzman et al.

(10) Patent No.: US 6,426,227 B1
(45) Date of Patent: Jul. 30, 2002

(54) METHOD FOR ANALYZING SECRETED BODILY FLUIDS

(75) Inventors: Amnon Kritzman, Zichron Yaakov; Alex Schoenfeld, Tel Aviv; Bonstein Lilach, Zichron Yaakov, all of (IL)

(73) Assignee: Common Sense Ltd., Industrial Park (IL)

( * ) Notice: Subject to any disclaimer, the term of this patent is extended or adjusted under 35 U.S.C. 154(b) by 0 days.

(21) Appl. No.: 09/552,729

(22) Filed: Apr. 19, 2000

Related U.S. Application Data

(62) Division of application No. 09/386,346, filed on Aug. 31, 1999, now abandoned.

(51) Int. Cl.$^7$ .............................................. G01N 33/50
(52) U.S. Cl. ........................ 436/43; 436/63; 436/163; 436/169; 600/573; 600/584; 604/318; 604/358
(58) Field of Search ................................ 604/318, 330, 604/358, 361; 600/573, 584; 436/63, 43, 44, 169, 170

(56) References Cited

U.S. PATENT DOCUMENTS

| | | | | |
|---|---|---|---|---|
| RE24,666 E | * | 7/1959 | Draghi | 600/572 |
| 3,509,872 A | * | 5/1970 | Truhan | 122/31.1 |
| 3,850,160 A | * | 11/1974 | Denson | 600/572 |
| 3,934,575 A | * | 1/1976 | Bucalo | 435/287.7 |
| 5,063,930 A | * | 11/1991 | Nucci | 600/366 |
| 5,119,828 A | * | 6/1992 | Miller | 600/573 |
| 5,217,444 A | * | 6/1993 | Schoenfeld | 604/358 |
| 5,425,377 A | * | 6/1995 | Caillouette | 600/572 |
| 5,508,200 A | * | 4/1996 | Tiffany et al. | 422/66 |
| 5,769,813 A | * | 6/1998 | Peiler et al. | 604/11 |
| 5,823,953 A | * | 10/1998 | Roskin et al. | 600/309 |
| 5,876,389 A | * | 3/1999 | Bouchard et al. | 600/573 |
| 5,891,396 A | * | 4/1999 | Karl et al. | 422/63 |
| 6,106,461 A | * | 8/2000 | Roskin et al. | 600/309 |

* cited by examiner

*Primary Examiner*—Jeffrey Snay
(74) *Attorney, Agent, or Firm*—Winston & Strawn

(57) ABSTRACT

A method of analysis of vaginal secretions collected in an absorbent pad is disclosed. The method is effected by implementing the steps of (a) using an absorbent pad for collecting the vaginal secretions, the absorbent pad including an inner membrane for absorbing at least a portion of the secretion, the inner membrane being embedded among layers of the absorbent pad, and an external, viewable membrane including a color indicator for indicating a location of secretions absorbed by the absorbent pad according to at least one parameter being indicative of a pathological state; and (b) if the pathological state is indicated, biochemically analyzing the inner membrane at a location respective to the location of secretions absorbed by the absorbent pad for further characterizing the pathological state.

13 Claims, 6 Drawing Sheets

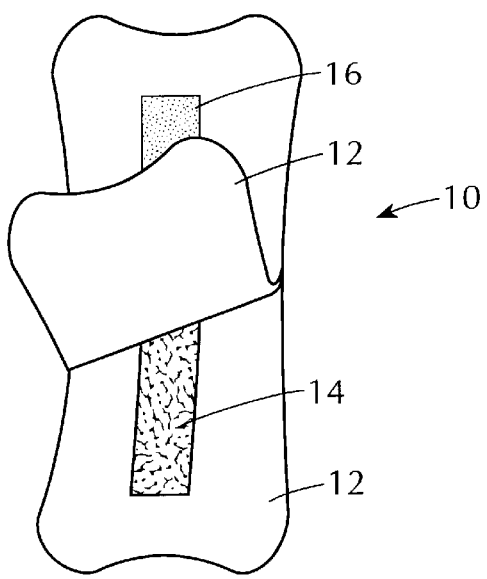
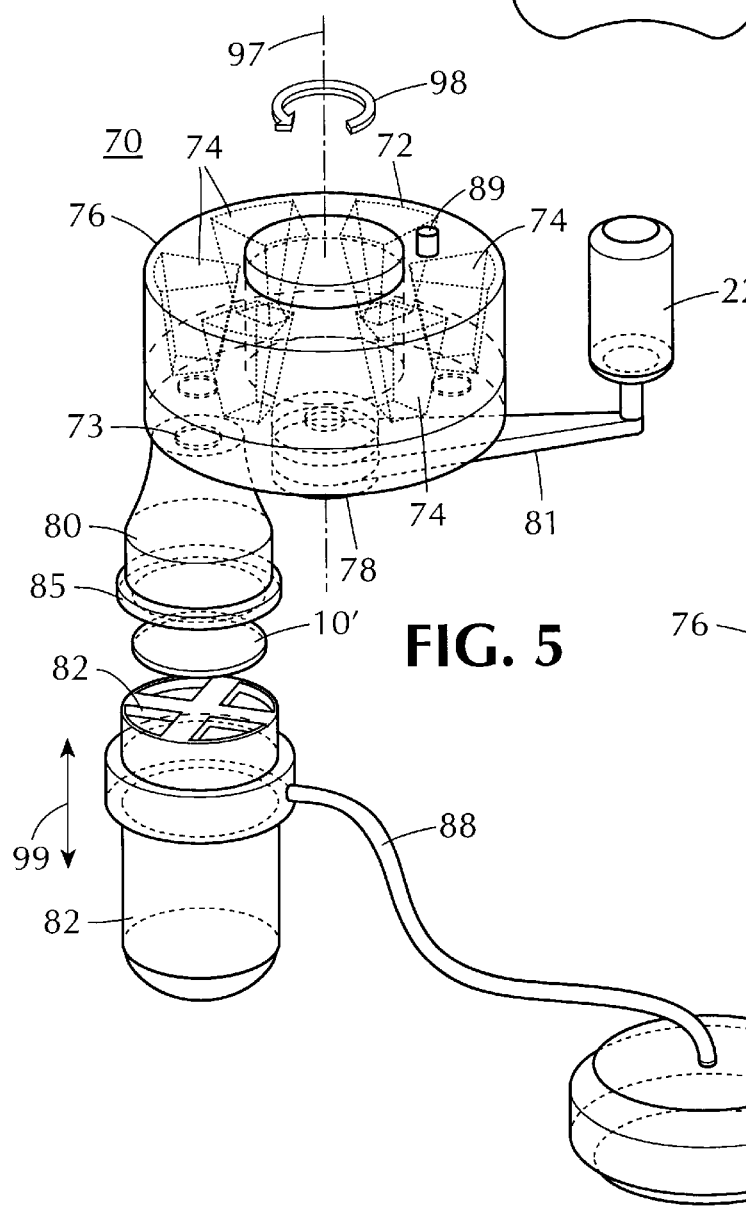
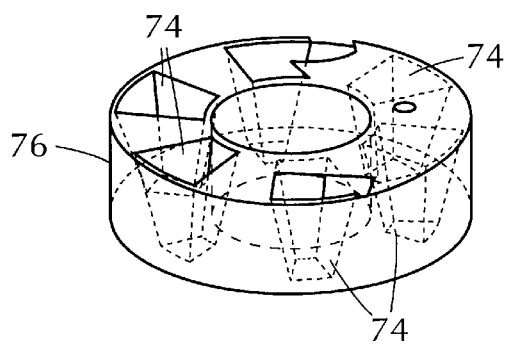

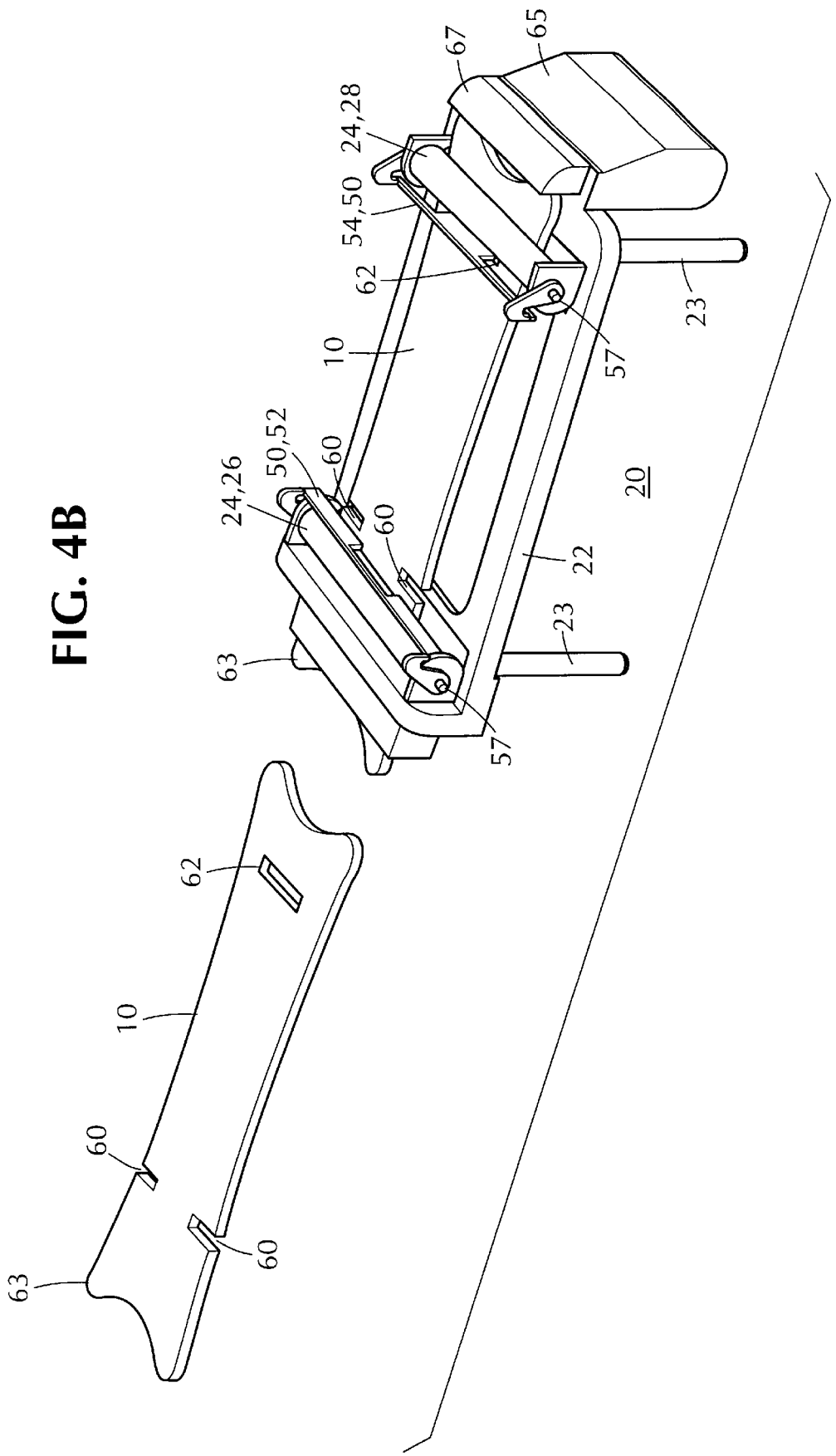

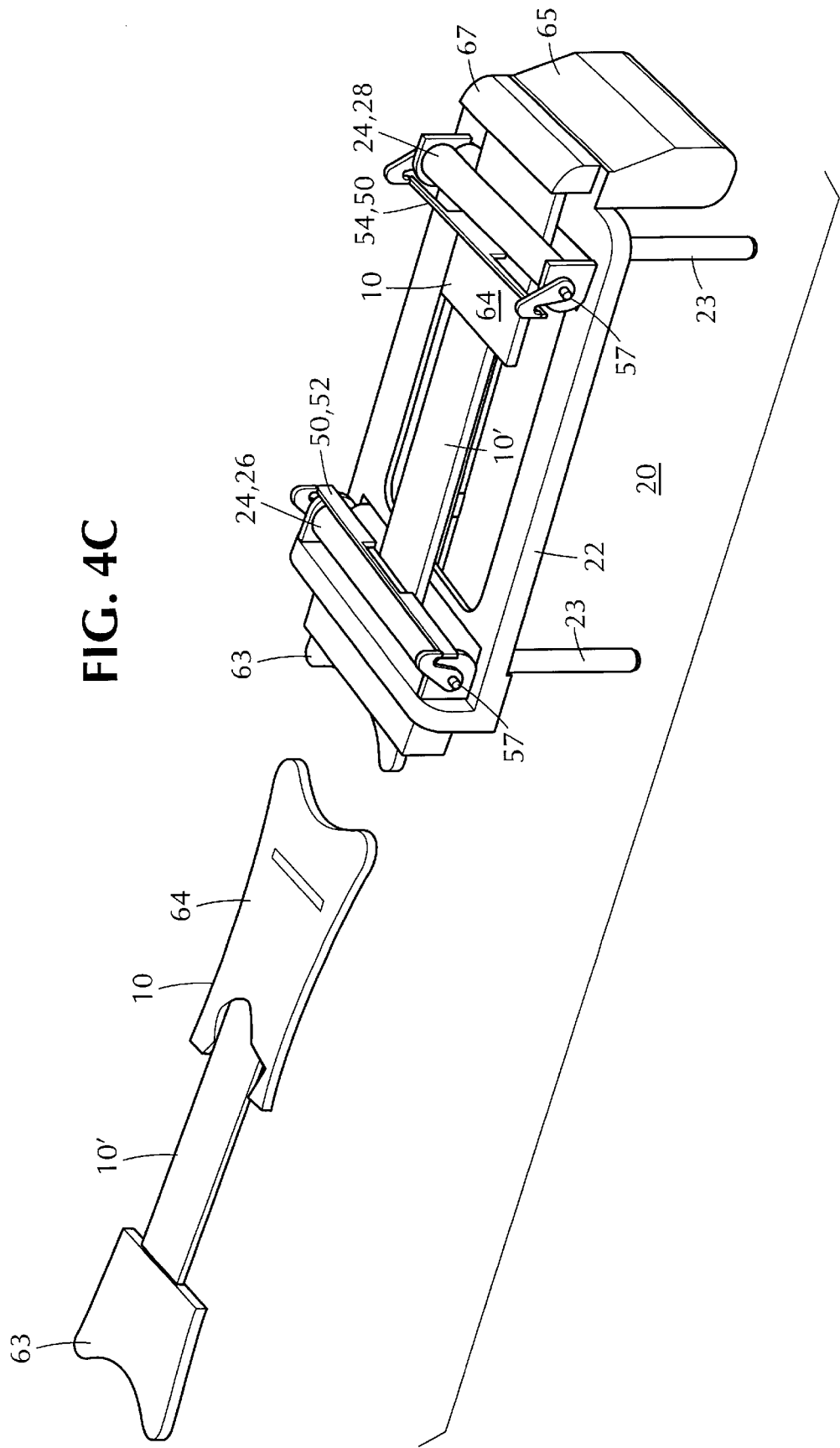

METHOD FOR ANALYZING SECRETED BODILY FLUIDS

This is a divisional of U.S. patent application Ser. No. 09/386,346, filed Aug. 31, 1999, now abandoned.

FIELD AND BACKGROUND OF THE INVENTION

The present invention relates to a device and method for analyzing bodily fluids of bodily secretions to diagnose a pathological state. More specifically, the present invention relates to a device and method for sampling bodily fluids collected by and contained in an absorbent pad and subsequently relaying the samples to an analyzer which performs a series of analytical tests either simultaneously or in sequence.

An early study of bacterial vaginosis (BV) involved comparisons of the pH of vaginal fluids of women known to be suffering from BV with those known to be free of the disease. Gardner, H. L., et al., Am. J. Obstet. Gynecol. 69:962 (1955). All of the BV positive women in the study were determined to have a vaginal fluid pH greater than 4.5, and 91% of these women had a vaginal fluid pH greater than 5.0. Of the normal (disease-free) women in the test, 92% were found to have vaginal pH between 4.0 and 4.7. The conclusion drawn from the study was that a vaginal pH equal to or greater than 5.0 in conjunction with other clinical criteria was indicative of the presence of BV.

Subsequent studies culminating by Amsel, R., et al., Am. J. Med. 74:14–22 (1983), resulted in a reduction of the pH threshold for BV to 4.5, and established the remaining criteria as vaginal fluid homogeneity, the whiff test (treatment with alkali followed by an olfactory test to detect for an amine odor), and the presence of clue cells. These are commonly referred to as the Amsel clinical criteria for BV. The conclusion was based on a study group of 397 women in which 81% of BV positive women were found to have a pH greater than 4.5 while only 23% of the normal women were found to have a vaginal fluid pH greater than 4.5.

Studies subsequent to the report by Amsel et al. have now adjusted the pH threshold to 4.7. One of these is the study of Holst, E., J. Clin. Microbiol. 28:2035–2039 (1990), in which 100% of the women diagnosed as BV positive by the Amsel criteria were reported to have vaginal fluid pH greater than 4.7. Another is the study by Eschenbach, D. A., Am. J. Obstet. Gynecol. 158(4):819–828 (1988), in which all 257 women in the study group who had at least 20% clue cells were shown to have a vaginal fluid pH greater than or equal to 4.7, leading to the conclusion that a threshold value of 4.7 correlated best with the other clinical evidence of BV. Krohn, M. A., et al., J. Clin. Microbiol. 27(6):1266–1271 (1989), also verified the correlation between the vaginal fluid pH threshold of 4.7 and the presence of clue cells, and Holmes, K. K., and coworkers further confirmed the pH 4.7 threshold as an indicator of BV—Holmes, K. K., et al., eds., Sexually Transmitted Diseases, McGraw-Hill, New York (1990), Chapter 46:527–545 (Holmes, K. K., et al.), and Chapter 47:547–559 (Hillier, S. L., et al.).

The whiff test, which is one of the Amsel criteria, originated in a study by Pheifer, et al., N. Engl. J. Med. 298:1429–1434 (1978), that reported the presence of a characteristic fishy amine odor upon the addition of 10% KOH to a vaginal fluid specimen from a woman with BV. The odor is caused by the alkaline volatilization of amine salts found in the vaginal fluid of women with BV. Unfortunately, the test is highly subjective, it exposes the health care worker to potential biological hazards, and it is disagreeable and vulnerable to error, since it is performed on a microscope slide which, due to the transient nature of the amine odor, must be placed directly under the nose and sniffed immediately after the addition of the KOH.

Alternatives to the whiff test are analytical procedures such as high voltage electrophoresis (Chen, K. C. S., et al., J. Clin. Invest. 63:828–835 (1979)), thin-layer chromatography (Chen, K. C. S., et al., J. Infect. Dis. 145:337–345 (1982), and Sanderson, B. E., et al., Br. J. Vener. Dis. 59:302–305 (1983)), gas chromatography (Gravett, M. G., et al. Obstet. Gynecol. 67:229–237 (1986), and Dravenieks, A., et al., J. Pharma. Sc. 59:495–501 (1970)), and high-performance liquid chromatography (Cook, R. L., et al., J. Clin. Microbiol. 30:870–877 (1992)). These procedures, although more accurate and reliable than the whiff test, are expensive, time-consuming, and not suitable for on-site testing in a physician's office or clinic.

Clue cells, which constitute a further Amsel criterion, are independently correlated with BV, and in the hands of a skilled microscopist are a very sensitive and specific indication of this infection. Clue cells are squamous vaginal epithelial cells found in vaginal fluid when BV is present. The cells are covered with numerous bacteria, giving them a stippled or granular appearance, and their borders are obscured or fuzzy because of the adherence of numerous rods or cocci. According to standard clinical practice, a diagnosis of BV is established when at least 20% of the detectable epithelial cells are clue cells. Holmes, et al., Sexually Transmitted Diseases, 2d ed., McGraw-Hill, Inc., New York, 1990.

Distinguishing between true clue cells in which the adherent bacteria completely obscure the edges of the cells and cells with simply a few adherent bacteria requires training and experience. One source of error is similarity in appearance between clue cells and trichomonads, white blood cells and other vaginal fluid components, frequently resulting in an incorrect identification of these cells as clue cells, and therefore false positive test results. Another is that clue cells when present are frequently obscured by numerous vaginal fluid components causing the clinician to miss the clue cells completely or to quantify them at levels below their actual level. This can result in a false negative test result. Therefore, it would be highly desirable to have a distinct analyte that is accurately and conveniently monitored and whose presence is correlated with clue cells.

U.S. Pat. No. 5,217,444 to Schoenfeld teaches an absorbent pad, for use in absorbing secretions from a person's body, which includes a pH indicator material indicating by a color change the acidity or alkalinity of a liquid coming into contact with it. The pH indicator material is wetted by the secretions absorbed by the pad, and thereby provides an indication of the health condition of the person's body.

U.S. Pat. No. 5,853,669 to Wolfbeis teaches a hydrophilic accommodating layer disposed on a hydrophobic mechanically stable support element, which layer contains an indicator dye in an immobilized form for the purpose of visual or optical indication of the pH of a sample which can be used as the pH indicator in the pad of Schoenfeld and in other applications as well.

The prior art teaches devices which, upon contact with liquid bodily secretions, has the capacity to change color by virtue of a pH indicator contained in the device. To this end, see U.S. Pat. Nos. 5,217,444 which is further described above and 5,769,813. In many cases an aberrant pH is an indication of a pathological state, for example an infection by a pathogen. Although the aforesaid prior art device indicates that there is a need for a specific medical diagnosis, it does not provide such a diagnosis. It does, however, suggest that there is sufficient biological material contained in the absorbent material of a tampon or hygienic pad to be used for medical diagnostics. This is especially true if analytical methods such as PCR or ELISA, which have signal amplification as inherent properties, are employed to make a final diagnosis.

Use of vaginal secretions contained in an absorbent pad (tampon or hygienic pad) offers a number of advantages when compared to other methods of obtaining samples of the same secretion. For example, most patients are capable of inserting and removing such a pad without aide. This means that a sample can be obtained without a gynecological examination. In addition, a patient suspecting an infection could bring or send a pad containing a sample to her doctor, making a subsequent appointment to receive the results and a prescription for treatment, if so required. This reduces the number of necessary medical appointments, an advantage for both patient and doctor. In some situations, for example patients living in remote areas, it is conceivable that a pad containing a sample would be mailed to a medical center, with results and prescription being returned by phone or fax.

The prior art also teaches pads with devices for collecting blood (U.S. Pat. No. Re:29,061) and for testing for microorganisms (U.S. Pat. No. 3,934,575) contained therein.

The present invention represents an improvement on the aforesaid prior art devices because it facilitates automated and detailed diagnosis or diagnoses from a single pad.

Automated sampling devices are known in the prior art. U.S. Pat. No. 4,120,662, for example, teaches a device which can withdraw liquid samples from a series of reservoirs loaded into a rack via the use of robotics. U.S. Pat. No. 5,846,490 teaches a device which automatically supplies test strips to an analyzing device. U.S. Pat. No. 5,865,975 teaches a device which automatically performs electrophoretic analysis of DNA fragments. U.S. Pat. Nos. 4,994,751; 5,154,889 and 5,425,918 teach additional devices for automated fluid analysis, chemical analysis and immunohistochemical analysis. The above listed patents are incorporated herein by reference.

However, all of the devices disclosed in the prior art are structurally and functionally inadequate for automatically collecting and thereafter analyzing vaginal secretions from an absorbent pad such as a hygienic pad or tampon.

There is thus a widely recognized need for, and it would be highly advantageous to have, an automated device for diagnosis of vaginal or cervical pathologies via analysis of secretions found in an absorbent pad such as a hygienic pad or tampon.

SUMMARY OF THE INVENTION

According to one aspect of the present invention there is provided a device for automatic analysis of bodily secretions collected in an absorbent pad, the device comprising (a) a platform; (b) a first mechanism being supported by the platform for accepting, holding and advancing the absorbent pad along the platform; (c) a second mechanism being supported by the platform for identifying at least one location being suitable for the analysis; (d) a third mechanism being supported by the platform for exposing a portion of the absorbent pad; and (e) a fourth mechanism being supported by the platform for performing a biochemical analysis of the bodily secretions present in at least one of the locations.

According to further features in preferred embodiments of the invention described below, the device is further for subsequent disposal of the pad, the device further comprising a disposal chamber for accepting the absorbent pad following the biochemical analysis.

According to still further features in the described preferred embodiments the first mechanism for accepting, holding and advancing the absorbent pad includes a proximal rolls unit and a distal rolls unit, each of the proximal and distal rolls units includes a roll biased against the platform, so as by controllably rolling the rolls, the first mechanism functions so as to accept, hold and advance the absorbent pad along the platform.

According to still further features in the described preferred embodiments the third mechanism for exposing a portion of the absorbent pad includes a proximal cutting unit and a distal cutting unit, each of the proximal and distal cutting units includes a moveable cutting element contactable with the absorbent pad, so as to form cuts in the absorbent pad, to thereby assist in exposing the portion of the absorbent pad.

According to still further features in the described preferred embodiments the portion is a membrane disposed within layers of the pad, the proximal and distal cutting units are so designed so as to form the cuts such that most of the remaining portions of the absorbent pad are removable by the first mechanism.

According to still further features in the described preferred embodiments the device further comprising a bridge translatable along the platform, the bridge serves for carrying both the second mechanism for identifying the at least one location suitable for the analysis and the fourth mechanism for performing the biochemical analysis of the bodily secretions present in at least one of the locations.

According to still further features in the described preferred embodiments the second mechanism for identifying the at least one location suitable for the analysis includes an optical sensor for sensing a color developed on the absorbent pad at a location of collected secretion.

According to still further features in the described preferred embodiments the color develops in response to pH.

According to still further features in the described preferred embodiments the fourth mechanism for performing the biochemical analysis of the bodily secretions present in at least one of the locations includes (i) a cartridge engaged on the bridge, the cartridge includes an opening and a plurality of moveable reservoirs moveably positionable against the opening so as to discard a liquid reagent content thereof through the opening; (ii) a funnel leading liquids from the opening to a surface of the portion of the absorbent pad at one of the at least one locations; and (iii) a suction operated liquid collecting and retaining container contactable with an opposite surface of the portion of the absorbent pad at one of the at least one locations; the liquid reagent content of the plurality of reservoirs are selected such that ordered application and removal thereof onto the portion of the absorbent pad at one of the at least one locations results in a developed indication which relates to the biochemical analysis.

According to still further features in the described preferred embodiments the reservoirs include at least one reagent selected from the group consisting of a primary antibody, a secondary antibody, a blocking reagent, a color reagent and a wash reagent.

According to another aspect of the present invention there is provided a method of analysis of vaginal secretions collected in an absorbent pad, the method comprising the steps of (a) using an absorbent pad for collecting the vaginal secretions, the absorbent pad including an inner membrane for absorbing at least a portion of the secretion, the inner membrane being embedded among layers of the absorbent pad, and an external, viewable membrane including a color indicator for indicating a location of secretions absorbed by the absorbent pad according to at least one parameter being indicative of a pathological state; and (b) if the pathological state is indicated, biochemically analyzing the inner membrane at a location respective to the location of secretions absorbed by the absorbent pad for further characterizing the pathological state.

According to further features in preferred embodiments of the invention described below, the at least one parameter is a pH value of the vaginal secretions.

According to still further features in the described preferred embodiments the pathological state is bacterial vaginosis.

According to still further features in the described preferred embodiments the step of biochemically analyzing the inner membrane is effected by an immunoassay.

According to still further features in the described preferred embodiments the step of biochemically analyzing the inner membrane at the location respective to the location of secretions absorbed by the absorbent pad for further characterizing the pathological state is effected by a device for automatic analysis of bodily secretions collected in an absorbent pad which includes (a) a platform; (b) a first mechanism supported by the platform for accepting, holding and advancing the absorbent pad along the platform; (c) a second mechanism supported by the platform for identifying a location of the color indicator if the pathological state is indicated by the color indicator; (d) a third mechanism supported by the platform for exposing at least a portion of the inner membrane; and (e) a fourth mechanism being supported by the platform for performing the step of biochemically analyzing the inner membrane at the location respective to the location of secretions absorbed by the absorbent pad.

According to still further features in the described preferred embodiments the first mechanism for accepting, holding and advancing the absorbent pad includes a proximal rolls unit and a distal rolls unit, each of the proximal and distal rolls units includes a roll biased against the platform, so as by controllably rolling the rolls, the first mechanism functions so as to accept, hold and advance the absorbent pad along the platform.

According to still further features in the described preferred embodiments the third mechanism for exposing the portion of the inner membrane includes a proximal cutting unit and a distal cutting unit, each of the proximal and distal cutting units includes a moveable cutting element contactable with the absorbent pad, so as to form cuts in the absorbent pad, to thereby assist in exposing the inner membrane.

According to still further features in the described preferred embodiments the device further includes a bridge translatable along the platform, the bridge serves for carrying both the second mechanism and the fourth mechanism.

According to still further features in the described preferred embodiments the second mechanism includes an optical sensor for sensing a color developed by the color indicator on the external membrane.

According to still further features in the described preferred embodiments the fourth mechanism includes (i) a cartridge engaged on the bridge, the cartridge includes an opening and a plurality of moveable reservoirs moveably positionable against the opening so as to discard a liquid reagent content thereof through the opening; (ii) a funnel leading liquids from the opening to a surface of the inner membrane; and (iii) a suction operated liquid collecting and retaining container contactable with an opposite surface of the inner membrane; the liquid reagent content of the plurality of reservoirs are selected such that ordered application and removal thereof onto the inner membrane results in a developed indication which relates to the biochemical analysis.

According to still further. features in the described preferred embodiments the device further includes a fifth mechanism supported by the platform for monitoring immunoassay produced fluorescence.

According to still further features in the described preferred embodiments the second mechanism also serves for detection of an ELISA produced color spot.

The present invention successfully addresses the shortcomings of the presently known configurations by providing a device and method for analyzing bodily fluids of bodily secretions to diagnose a pathological state. In particular, the present invention successfully addresses the shortcomings of the presently known configurations by providing an integrated device and method for analyzing bodily fluids which are collected into an absorbent pad.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most usefull and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1. is a perspective view of a hygienic pad according to the present invention;

FIGS. 4a–c are perspective views of the lower portion of the device according to the present invention in three successive steps when handling a pad, wherein the handled pad is shown both engaged by the device (to the right) and as it would look if removed from the device at any given step (to the left);

FIG. 5 is a perspective view of a cartridge used in the device according to the present invention; and FIG. 6 is a perspective view of a holder which forms a part of the cartridge shown in FIG. 5.

DESCRIPTION OF THE PREFERRED EMBODIMENTS

Figure 2:
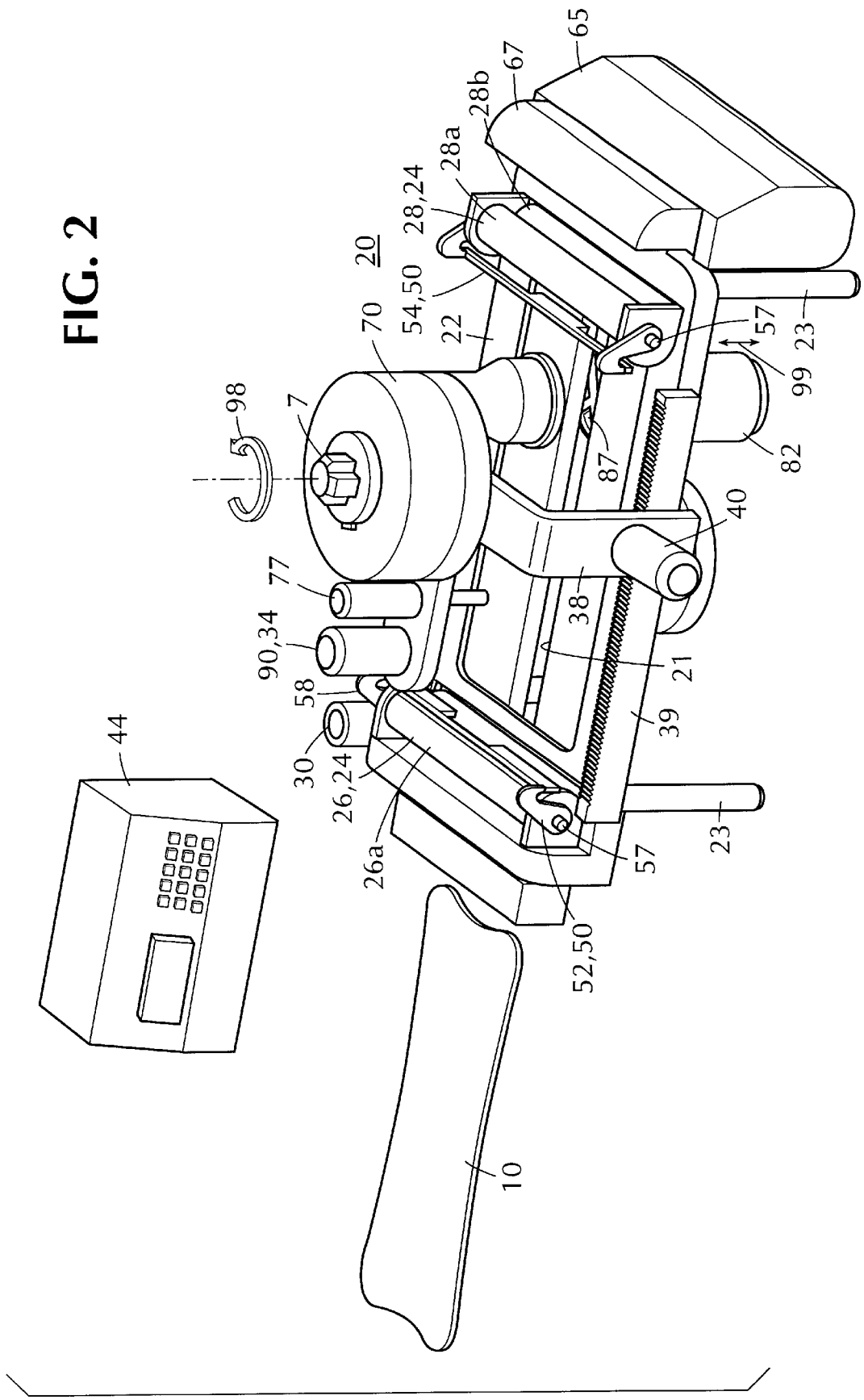
FIG. 2 is a perspective view of a device according to the present invention.
Figure 3:
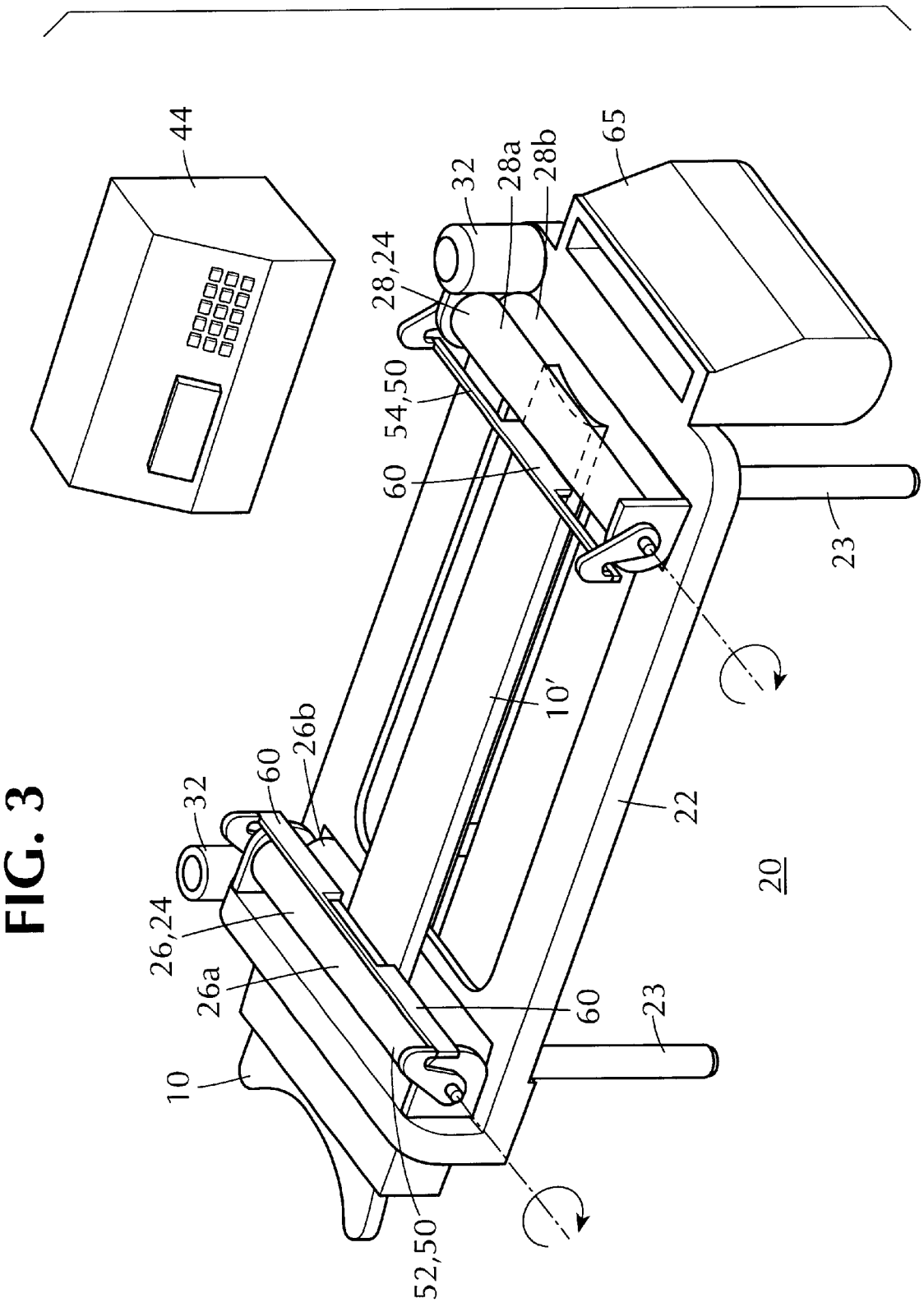
FIG. 3 is a perspective view of a lower portion of the device shown in FIG. 2.

The present invention is of a device and method for sampling bodily fluids collected by and contained in an absorbent pad and subsequently relaying the samples to an analyzer which performs a series of analytical tests either simultaneously or in sequence.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

U.S. Pat. No. 5,217,444, which is incorporated herein by reference teaches an absorbent pad for use in absorbing secretions from a person's body, which includes a pH indicator material indicating by a color change the acidity or alkalinity of a liquid coming into contact with it. The pH indicator material is wetted by the secretions absorbed by the pad, and thereby provides an indication of the health condition of the person's body. The object of the invention described in the above patent is to provide a method and means which can be conveniently examined by the user to provide an early indication of the health condition of the user's body, particularly whether there may be an infectious cause for a vaginal discharge.

In accordance with the teachings of U.S. Pat. No. 5,217,444, there is provided a tampon for use in absorbing secretions from a person's body, particularly vaginal discharge, characterized in that the tampon includes a pH indicator material indicating by a color change the acidity or alkalinity of the secretion coming into contact with the material, the pH indicator material being included in the tampon so as to be wetted by the secretions absorbed by the tampon, thereby providing an indication of the health condition of the person's body. Preferably, the tampon includes a plurality of pH indicator materials each producing a color change at a different pH value, to provide a more precise indication of the specific pH value, to provide a more precise indication of the specific pH value of the secretion absorbed by the tampon, and thereby a better indication of the health condition of the user. The pH indicator material may be impregnated in a fibrous strip bonded to the tampon such as to be wetted by the secretions of the person's body absorbed by the tampon; alternatively, the pH indicator material may be impregnated in at least a portion of the tampon such as to be wetted by the secretions of the person's body absorbed by the tampon. The users of such tampons would be instructed to visually inspect the color of the tampon, or the portion thereof carrying the pH indicator material, and if a certain color change occurred, to immediately seek an examination by the user's physician in order to make the further tests required in order to diagnose the cause of the secretion, and particularly whether it is an infectious cause. For example, a normal vaginal discharge has a pH of less than 4.5, whereas a pH of greater than 5.0 indicates the possibility of the presence of Trichimonas vaginalis or Bacterial vaginosis. Therefore, if the pH indicator material applied to the tampon produced a color change between pH 4.5 and 5.0, this indicates the possibility of one of these infections. The user could visually inspect the color of the tampon after its use and if such a color change occurred, indicating the possibility of one of these infectious causes for the vaginal discharge, she would be immediately alerted to see her physician to enable further tests to be performed so as to determine the precise reason for the discharge.

However, U.S. Pat. No. 5,217,444 fails to teach further diagnosis of the health condition of the user, which is the subject of the present invention.

For purposes of this specification and the accompanying claims the term "bodily fluids" refers primarily to vaginal secretions, for example non-menstrual blood secretions, but also includes other vaginal secretions and exudates such as menstrual blood secretions as well as urine, feces, wound exudates, ear exudates, saliva, tears and nasal mucous.

Referring now to the drawings, FIG. 1 illustrates an absorbent pad 10 which can be used for implementing the method of the present is invention according to a preferred embodiment thereof. Thus, pad 10, which is shown in FIG. 1 to be a hygienic pad, includes layers 12 of absorbent material. Absorbent pad 10 typically includes a plurality of absorbent layers packed together into a form having a high absorbing capacity. Pad 10 further includes an inner membrane 14 (which is referred to herein below also as portion 10') which serves for absorbing at least a portion of the vaginal secretions. Inner membrane 14 is embedded among layers 12 of absorbent pad 10. An external, viewable membrane 16 which includes a color indicator is externally applied to pad 10 and serves for indicating a location of secretions absorbed by absorbent pad 10 according to at least one parameter which is indicative of a pathological state. It will be appreciated that external membrane 16 serves not only to indicate a pathological state, it also serves to indicate a suitable location for biochemical analysis of the vaginal secretions, as is further detailed below.

Although FIG. 1 shows a hygienic pad, it is to be understood that the present invention is not limited to such a pad in particular. For example, a tampon can be employed in some applications. Furthermore, in its broader aspect, the present invention is not limited to absorbent pads employed for female hygiene, rather it encompasses all other pads made of absorbent materials, such as a wound dressing, a bandage, a swab, a sponge, a dipper, a tissue an absorbent strip and the like.

According to the present invention, if a pathological state is indicated via the color indicator of external membrane 16, inner membrane 14 is biochemically analyzed to further characterize the pathological state. A preferred location for analysis is selected according to a color spot which develops on external membrane 16 by means of the color indicator. Such a spot may, for example, indicate of a substantial amount of absorbed secretion which is most suitable for biochemical analysis. Membranes 14 and 16 are preferably centered and are positioned along a longitudinal axis of pad 10. In some embodiments membranes 14 and 16 are integrated into a single membrane which serves both functions.

According to a preferred embodiment of the present invention the at least one parameter is a pH value of vaginal secretions. As further detailed in the Background section above, the pH value of vaginal secretions is indicative of the presence or absence of bacterial vaginosis. Thus, according to a preferred embodiment of the present invention the color indicator is a pH color indicator which is sensitive to subtle pH changes in the appropriate pH range for detecting bacterial vaginosis. Further details relating to suitable pH indicators and their addition to a membrane are discussed in U.S. patent application No. 09/372,571, filed Aug. 12, 1999, entitled "PH SENSOR FOR INDICATING THE PH OF A SAMPLE, THE FABRICATION AND USE THEREOF" which is incorporated by reference as if fully set forth herein.

However, the present invention is not limited to pH indicators. The prior art teaches a plurality of other indicators for detecting a variety of substances, their presence in a bodily secretion is indicative of a pathological state which is ought to be further analyzed. For example, membranes, membranes for urine examination which detect urobilinogen, bilirubin, nitrite, blood, blood fang, leukocytes, protein, glucose, ascorbic acid or keton bodies are available from Behring (Germany) Bayer (Switzerland) and/or Ames (USA). In addition, U.S. Pat. Nos. 5,902,731; 5,789,255 and 5,871,695, which are incorporated herein by reference, teach various diagnostic strip reagents.

Pad 10 is employed either during routine use or in a dedicated attempt to collect bodily fluids. Pad 10 is placed in position by the patient for collection of bodily fluids. When sufficient fluid has been collected, pad 10 is preferably sealed in a bag and is thereafter delivered to a physician or to a medical center for analysis as is further detailed herein.

It will be appreciated that for some of the tests further listed below, a delay in examination does not affect the results. Under such circumstances, pad 10 can be mailed for analysis using conventional mailing services.

Any one of a plurality of biochemical methods can be employed while analyzing the vaginal secretions collected by pad 10. Examples include, but are not limited to, polymerase chain reaction (PCR), ligase chain reaction (LCR), reverse transcriptase—polymerase chain reaction (RT-PCR), immunoassay such as, fluorescent immunoassay, enzyme linked immunosorbent assay (ELISA) or radio immuno assay (RIA), fluorescence activated cell sorting (FACS), gel electrophoresis, microscopy, Immuno-fluorescence, SNIRPS analysis and/or restriction fragment length polymorphism (RFLP) analysis. These methods are well known in the art and require no further description herein. Devices for executing such procedures are also well known. It is expected that during the life of this patent many relevant medical diagnostic techniques will be developed and the scope of the present invention is intended to include all such new technologies a priori.

In any case, and as is further detailed herein, a presently preferred biochemical analysis method is a fluorescent immunoassay. Such an assay is known to be a highly sensitive method in detecting minute quantities of a specific biological material present in a sample. Such an assay can be calibrated to perform either qualitatively or quantitatively. The high sensitivity of such an assay is due to synergetic operating factors. The first factor is the use of a primary antibody which stoichiometrically, specifically and efficiently binds to a biological material of interest present in a sample. The second, is the use of a signal amplification mechanism which employs in the case of a fluorescent immunoassay a secondary antibody which recognizes the primary antibody and which is fluorescently tagged.

The method according to the present invention can be performed manually. In other words, once a pathological state is observed due to color development at least one spot of external membrane 16, inner membrane 14 is analyzed by any of the above methods, wherein the location for analysis is selected respective to one of the spots formed on external membrane 16. Devices which are applicable these assays are well known. For example, a dot blot device can be used to perform an immunoassay. Such a device is known to include two elements which connect in a sealing relation while a membrane is disposed therebetween, such that a chamber for accepting liquids is formed above the membrane and vacuum is applyable therebelow. The assay is performed by sequential application of reagents to the chamber, incubation, and removal of the reagents by suction. The following sequence of reagent application may be useful. First a wash reagent is used to wash away access, non-bound, material from the membrane. This procedure can be repeated one or several times. Second, a blocking reagent is incubated for say 5 to 15 minutes with the membrane and its access thereafter removed by suction. The membrane is washed again. Then, a primary antibody is incubated for say 5 to 15 minutes with the membrane and its access thereafter removed by suction. The membrane is washed again. Then, a secondary, fluorescently tagged, antibody is applied, incubated and removed. After a final wash, the membrane bound fluorescence is monitored. A similar sequence of events is effected while implementing ELISA, except that in this case the secondary antibody is tagged by an enzyme, such as alkaline phosphatase, which is capable of catalyzing a colorimetric reaction. In this case, an additional, color reagent is applied following the secondary antibody, which reagent includes substrates which cause color formation if the enzyme is present. In any case, following a final wash, the reaction is monitored. If fluorescent secondary antibody is employed, the analysis involves illumination with a light including an exiting wavelength and detection of fluorescence at the emission wavelength. If an enzyme tagged secondary antibody is employed, the results can be monitored by the naked eye or an optical reader. It will be appreciated that primary antibodies are commercially for all of the common vaginosis pathogens, including, but not limited to, candida, chlamydia, trichomonas and gonorrhea. Similarly, fluorescently or enzyme tagged secondary antibodies, capable of binding these primary antibodies, are also available commercially, for example, secondary antibodies labeled with the fluorophore R-Phycoerythrin (RPE) which is exited at 488 nm and emits at 575 nm.

However, according to preferred embodiments, the method of the present invention is executed automatically by a dedicated device which forms another aspect of the present invention and which is further described hereinunder with reference to FIGS. 2–5.

Thus, according to another aspect of the present invention there is provided a device for automatic analysis of bodily secretions collected in 10, which is referred to hereinbelow as device 20.

Device 20 according to this aspect of the present invention includes a platform 22 which is formed with a central opening 21 and which is elevated, e.g., by elevating legs 23, so as to allow access there underneath. Device 20 further includes a first mechanism 24 which is supported by platform 22 and which serves for accepting, holding and advancing absorbent pad 10 along platform 22.

According to a preferred embodiment of the present invention first mechanism 24 which serves for accepting, holding and advancing absorbent pad 10 along platform 22 includes a proximal rolls unit 26 and a distal rolls unit 28. Each of proximal 26 and distal 28 rolls units includes a first roll 26a and 28a, respectively, biased against platform 22 or alternatively against a second roll 26b and 28b, respectively, such that by controllably rolling rolls 26a–b and/or 28a–b, via motors 30 and 32 respectively, first mechanism 24 functions so as to accept, hold and advance absorbent pad 10 or, as further detailed hereinunder, portions thereof, along platform 22. At other instances, and for reasons which will become apparent reading the following paragraphs, first mechanism 24 serves to hold pad 10 or portions thereof stationary. It will be appreciated that first mechanism 24 can be alternatively realized by, for example, a pair of conveyer belts running along the sides of platform 22 or the like.

Device 20 further includes a second mechanism 34 which is supported by platform 22 and which serves for identifying at least one location on pad 10 which is suitable for analysis. Second mechanism 34 which, as stated, serves for identifying at least one location suitable for further analysis, includes an optical sensor 36 which serves for scanning and sensing a color developed on absorbent pad 10 at a location of collected secretion and which is suitable for biochemical analysis. Optical sensor 36 can be, but is not limited to, a camera, such as a video or digital camera, or an optical scanner. In a preferred embodiment a simple monochromatic optical scanner is employed for locating a location suitable for further biochemical analysis. Such a location is identified, for example, by the presence of a color change of a pH indicator, which, as is further detailed hereinabove, is indicative of a pathological state. Thus, as is further detailed hereinabove, when absorbent pad 10 is a hygienic pad as shown in FIG. 1, such a color may develop in cases of bacterial vaginosis on membrane 16 as a response to a subtle pH change in the vaginal secretions. Such a spot can be identified through a bag containing pad 10 provided that the bag is transparent.

Second mechanism 34 is carried on a translating bridge 38 translatable along platform 22 via a motor 40 and which is guided along a toothed rail 39 which is disposed along a length of platform 22. Thus, following the insertion of pad 10 into device 20 via rolls unit 26 and the advancement thereof in a direction of rolls unit 28, and its fixation by units 26 and 28 over platform 22, pad 10 is scanned by translating bridge 38 along platform 22. The coordinates of location or locations suitable for analysis are recorded and memorized by a computerized control unit 44 which is preferably wired to or alternatively remotely communicating with device 20.

According to a preferred embodiment, when received for examination, a pad 10 is marked by a bar-code sticker adhered thereto, which bar-code is associated with a patient. The bar-code is preferably also scanned by second mechanism 34 and is correlated to the results obtained thereafter, so as to prevent patient mis-identification. All patient related information including the patient's identification are preferably recorded into a memory of control unit 44 for later retrieval.

Device 20 further includes a third mechanism 50 which is supported by platform 22 and which serves for exposing a portion 10' of absorbent pad 10. In a preferred embodiment of the invention portion 10' is an inner membrane such as membrane 14 which is shown in FIG. 1.

According to a preferred embodiment of the present invention, third mechanism 50 which serves for exposing portion 10' of absorbent pad 10 includes a proximal cutting unit 52 and a distal cutting unit 54. Each of proximal 52 and distal 54 cutting units includes a moveable cutting element 56 which is operated by a motor 58 and which is contactable with absorbent pad 10, so as to form cuts in absorbent pad 10, to thereby assist in exposing portion 10' of absorbent pad 10. Motor 58 is rotatable about a hinge 57.

Figure 4A:
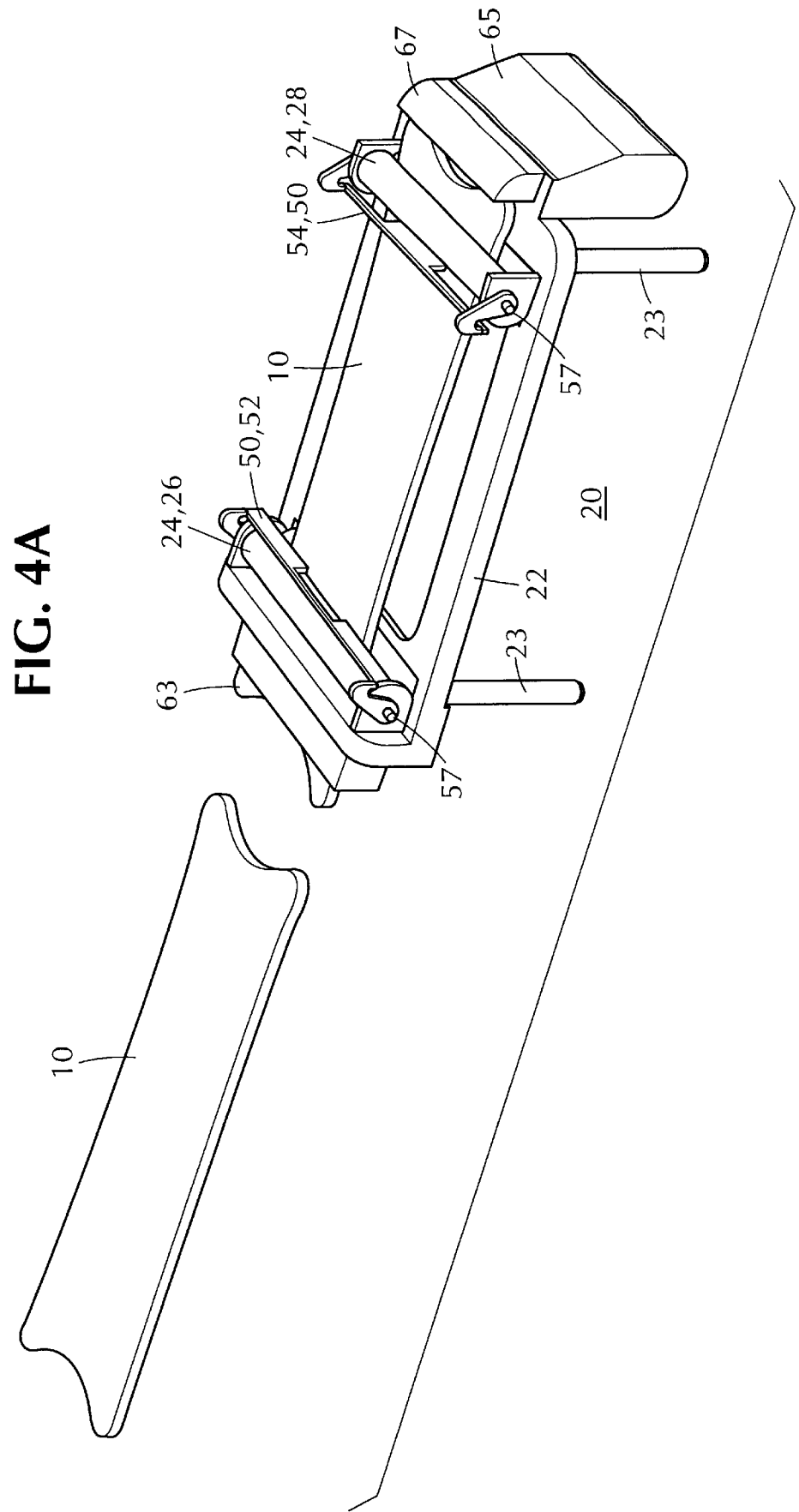

FIGS. 4a–c demonstrate the process of exposing portion 10' of absorbent pad 10 according to this embodiment of the present invention. Thus, one coordinates for at least one suitable analysis location have been established by second mechanism 30, third mechanism 50 is operated, as shown in FIG. 4b, to form two proximal side cuts 60 and a single distal central cut 62 through pad 10. Once cuts 60 and 62 have been formed, as shown in FIG. 4c, rolls unit 28 is operated to disconnect and remove a distal portion 64 of pad 10 to thereby expose portion 10' which is embedded within the layers pad 10, while rolls unit 26 serves at the same time to firmly hold stationary a proximal portion 63 of pad 10 and/or a proximal portion of portion 10' thereof, so as to assist in effecting the above described process. As a result, portion 10' is exposed for further analysis as further described herein.

Aided by unit 28, distal portion 64 of pad 10 is disposed into a cover protected 67 disposal chamber 65 which serves, at this stage, for accepting portion 64. As used herein the term "disposal" includes safe storage of bodily fluids and other biohazard materials until they can be removed for sterilization. Said safe storage occurs according to preferred embodiments of the present invention in chamber 65 which can be removed in its entirety and may also include chemical sanitizing agents, such as sodium hypochlorite solution, and may further include odorants or odor neutralizing materials such as activated charcoal. Active neutralization within chamber 65 is envisaged, as well known in the art.

Device 20 further includes a fourth mechanism 70 which is supported by bridge 38, itself translatably engaged by platform 22. Mechanism 70 serves for performing a biochemical analysis of bodily secretion present in at least one of the locations of pad 10 as was identified by the production of color indicative of a pathological state and second mechanism 30. Mechanism 70 is shown in greater detail in FIGS. 5–6 and it is therefore described mostly in context with these Figures.

Thus, fourth mechanism 70 which serves for performing the biochemical analysis of bodily secretion present on portion 10' of pad 10 includes a cartridge 72 engaged on bridge 38. Cartridge 72 includes an opening 74 and a plurality of moveable reservoirs 73 moveably positionable against opening 73, so as to discard a liquid reagent content thereof through opening 73. According to a preferred embodiment of the present invention reservoirs 74 are engaged within a holder 76 which forms a rotating part, as indicated by arrow 98 of cartridge 72 which is rotably connected to a stationary base portion 78 of cartridge 72. A locating mark such as a pin 89 is preferably used for maintaining an appropriate orientation between holder 76 and base 78 and/or between cartridge 72 as a whole and device 20. A motor 77 which is engaged by bridge 38 serves for rotating holder 76 relative to base 78 about a shaft 97 connected to bridge 38 which is designed to accept cartridge 72 through a central opening 79 formed thereat and to rotably engage holder 76, thereby to position different reservoirs 74 against opening 73, as is required from time to time. According to a preferred embodiment of the present invention a motor 77 which is engaged by bridge 38 serves for rotating holder 76 via belt transmission effected via a belt 81. It will however be appreciated that motor 77 can be a central motor replacing shaft 97.

Mechanism 70 further includes a funnel 80 or a similar mechanism which serves for leading liquids from opening 73 to a surface of portion 10' of absorbent pad 10. Mechanism 70 further includes a suction operated liquid collecting and retaining container 82 which is carried by a portion of bridge 38 being underneath platform 22 and which is contactable opposite to funnel 80 with an opposite surface of portion 10' of absorbent pad 10. Container 82 is supplemented with a supporting greed 87 for supporting portion 10' during analysis. Sealing rings 85 may be applied as required. A suction or vacuum device 86 which is in fluid communication via a tube 88 with container 82 serves to controllably apply suction to container 82.

As is further described hereinabove, the liquid reagent content of reservoirs 74, such as, but not limited to, a primary antibody, a secondary antibody, a blocking reagent, a color reagent and a wash reagent, are selected such that ordered application and removal thereof onto portion 10' of absorbent pad 10 at a selected location results in a developed color (conventional or fluorescence) indication which relates to the biochemical analysis.

To this end, as indicated by arrow 99, container 82 is vertically translatable so as to form sealing relation between container 82 and funnel 80.

If a fluorescent secondary antibody is employed, then, device 20 further includes a fifth mechanism 90 which serves for monitoring an immunoassay related fluorescent signal. Mechanism 90 includes a light source capable of radiating at the excitation wavelength of a fluorescent material and a light detector, capable of sensing fluorescent emission. Mechanism 90 is engaged by bridge 38 and is therefore translatable to any location along portion 10' of pad 10. The mechanical and optical operation of mechanism 90 is controlled by unit 44, which also serves to store the results.

On the other hand, if ELISA is employed, second mechanism 34 can be used, under the control of unit 44, to detect and or quantify the results, i.e., the ELISA related color development.

Aided by unit 28, and following the completion of the biochemical analysis and the interpretation and recordal of the results, portion 10', and any remaining portions of pad 10, such as proximal portion 63, are disposed into chamber 65.

Thus, according to preferred embodiments of the present invention device 20 operates as follows. A pad 10 is received and is inserted into device 20 aided by rolls unit 26. Pad 10 is inserted such that a color indication or spot formed on membrane 16 and which is indicative of a pathological state is accessible to second mechanism 30. Pad 10 is advanced by unit 26 along platform 22 and in then further engaged and retained stationary by units 26 and 28. At this stage, bridge 38 is translated and pad 10 scanned by second mechanism 30, so as to provide coordinates of one or more locations which are most suitable for biochemical analysis. Such locations are determined according to color formation thereat, which is indicative of a pathological state, as further detailed hereinabove. Once the coordinates are recorded and memorized by control unit 44, third mechanism 50 in combination with rolls units 26 and 28 of first mechanism 24 are employed to expose portion 10' of pad 10 and, at the same time, to dispose distal portion 64 of pad 10 into chamber 65. Measures are taken to ensure that portion 10' remains stationary, such that the recorded coordinates still apply thereto. Then, bridge 38 is translated so as to bring fourth mechanism 70 according to the recorded and memorized coordinates into position with a selected location of portion 10'. Holder 76 is then rotated with respect to base 78 of cartridge 72 so as to sequentially deliver the reagents contained in reservoirs 74 in contact with portion 10'. Suction device 86 is coordinately operated to sequentially remove following predetermined time intervals said reagents, so as to precisely execute the biochemical analysis. When the analysis has been completed, and typically following the interpretation of the results, either an additional analysis is performed at another location of portion 10', or alternatively, portion 10' and proximal portion 63 of pad 10 are disposed into disposal chamber 65, which process is aided by unit 28.

Control unit 44 is designed to automatically orchestrate the operation of the various mechanisms of device 20 so as to effect the above described analysis process. One of skills in the art would know how to program control unit 44 accordingly and how to appropriately and functionally connect between unit 44 and the various mechanism of device 20. Thus, the entire biochemical analysis process is fully automated thereby reducing exposure of operators to biologically hazardous materials. According to preferred embodiments of the present invention unit 44 is capable of performing at least one task, such as, for example, reporting to a central computer, e.g., via line communication or via the Internet or email, analysis of data related to an individual subject, statistical analysis relating to a plurality of subjects, and the like. Such information can be displayed on a display of unit 44. Any personal computer loaded with the appropriate software can serve the function of unit 44.

Some or all of the components of fourth mechanism 70, such as, for example, cartridge 72, funnel 80 and container 82, are preferably made disposable.

According to a preferred embodiment unit 44 is physically integrated into device 20 which is therefore rendered a readily portable device.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of analysis of vaginal secretions collected in an absorbent pad, the method comprising the steps of:
    (a) using an absorbent pad for collecting said vaginal secretions, said absorbent pad including an inner membrane for absorbing at least a portion of said secretion, said inner membrane being embedded among layers of said absorbent pad, and an external, viewable membrane including a color indicator for indicating a location of secretions absorbed by said absorbent pad according to at least one parameter being indicative of a pathological state; and
    (b) if said pathological state is indicated, biochemically analyzing said inner membrane at a location respective to said location of secretions absorbed by said absorbent pad for further characterizing said pathological state.

2. The method of claim 1, wherein said at least one parameter is a pH value of said vaginal secretions.

3. The method of claim 1, wherein said pathological state is bacterial vaginosis.

4. The method of claim 1, wherein said step of biochemically analyzing said inner membrane is effected by an enzyme linked immunosorbent assay.

5. The method of claim 1, wherein said step of biochemically analyzing said inner membrane at said location respective to said location of secretions absorbed by said absorbent pad for further characterizing said pathological state is effected by a device for automatic analysis of bodily secretions collected in an absorbent pad which includes
    (a) a platform;
    (b) a first mechanism supported by said platform for accepting, holding and advancing said absorbent pad along said platform;
    (c) a second mechanism supported by said platform for identifying a location of said color indicator if said pathological state is indicated by said color indicator;
    (d) a third mechanism supported by said platform for exposing at least a portion of said inner membrane; and (e) a fourth mechanism being supported by said platform for performing said step of biochemically analyzing said inner membrane at said location respective to said location of secretions absorbed by said absorbent pad.

6. The method of claim 5, wherein said first mechanism for accepting, holding and advancing said absorbent pad includes a proximal rolls unit and a distal rolls unit, each of said proximal and distal rolls units includes a roll biased against said platform, so as by controllably rolling said rolls, said first mechanism functions so as to accept, hold and advance said absorbent pad along said platform.

7. The method of claim 5, wherein said third mechanism for exposing said portion of said inner membrane includes a proximal cutting unit and a distal cutting unit, each of said proximal and distal cutting units includes a moveable cutting element contactable with said absorbent pad, so as to form cuts in said absorbent pad, to thereby assist in exposing said inner membrane.

8. The method of claim 5, wherein the device further includes a bridge translatable along said platform, said bridge serves for carrying both said second mechanism and said fourth mechanism.

9. The method of claim 8, wherein said second mechanism includes an optical sensor for sensing a color developed by said color indicator on said external membrane.

10. The method of claim 8, wherein said fourth mechanism includes:

(i) a cartridge engaged on said bridge, said cartridge includes an opening and a plurality of moveable reservoirs moveably positionable against said opening so as to discard a liquid reagent content thereof through said opening;

(ii) a funnel leading liquids from said opening to a surface of said inner membrane; and (iii) a suction operated liquid collecting and retaining container contactable with. an opposite surface of said inner membrane;

said liquid reagent content of said plurality of reservoirs are selected such that ordered application and removal thereof onto said inner membrane results in a developed indication which relates to said biochemical analysis.

11. The method of claim 10, wherein said reservoirs include at least one reagent selected from the group consisting of a primary antibody, a secondary antibody, a blocking reagent, a color reagent and a wash reagent.

12. The method of claim 5, wherein the device further includes a fifth mechanism supported by said platform for monitoring immunoassay produced fluorescence.

13. The method of claim 5, wherein said second mechanism also serves for detection of an ELISA produced color spot.

* * * * *

UNITED STATES PATENT AND TRADEMARK OFFICE
CERTIFICATE OF CORRECTION

PATENT NO.    : 6,426,227 B1  
DATED         : July 30, 2002  
INVENTOR(S)   : Amnon Kritzamn et al.

It is certified that error appears in the above-identified patent and that said Letters Patent is hereby corrected as shown below:

<u>Title page,</u>
Item [73], Assignee's address should read as follows:
-- Nazereth Illit, (IL) --.

Signed and Sealed this

Twelfth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,426,227 B1
DATED         : July 30, 2002
INVENTOR(S)   : Kirtzman et al.

It is certified that error appears in the above-identified patent and that said Letters Patent is hereby corrected as shown below:

<u>Title page,</u>
Item [73], Assignee: change "Industrial Park (IL)" to -- Nazereth Illit (IL) --.

Signed and Sealed this

Nineteenth Day of November, 2002

Attest:

Attesting Officer

JAMES E. ROGAN
*Director of the United States Patent and Trademark Office*